US010993688B2

(12) United States Patent
Carmi et al.

(10) Patent No.: US 10,993,688 B2
(45) Date of Patent: May 4, 2021

(54) METHOD OF DATA PROCESSING FOR COMPUTED TOMOGRAPHY

(71) Applicant: KONINKLIJKE PHILIPS N.V., Eindhoven (NL)

(72) Inventors: Raz Carmi, Haifa (IL); Liran Goshen, Pardes-Hanna (IL); Mordechay Pinchas Freiman, Zichron-Yaakov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 395 days.

(21) Appl. No.: 15/779,583

(22) PCT Filed: Dec. 7, 2016

(86) PCT No.: PCT/EP2016/079968
§ 371 (c)(1),
(2) Date: May 29, 2018

(87) PCT Pub. No.: WO2017/102467
PCT Pub. Date: Jun. 22, 2017

(65) Prior Publication Data
US 2020/0359985 A1    Nov. 19, 2020

(30) Foreign Application Priority Data

Dec. 15, 2015  (EP) .................................... 15200180

(51) Int. Cl.
*A61B 6/00* (2006.01)
*G06T 7/11* (2017.01)
(Continued)

(52) U.S. Cl.
CPC ............ *A61B 6/5258* (2013.01); *G06T 5/002* (2013.01); *G06T 7/0012* (2013.01); *G06T 7/11* (2017.01); *G06T 2207/10081* (2013.01)

(58) Field of Classification Search
CPC ..... A61B 6/5258; G06T 5/002; G06T 7/0012; G06T 7/11; G06T 2207/10081
(Continued)

(56) References Cited

U.S. PATENT DOCUMENTS

| 2002/0075997 | A1 | 6/2002 | Unger |
| 2008/0063135 | A1 | 3/2008 | Deman |

(Continued)

FOREIGN PATENT DOCUMENTS

| WO | 2014/128595 | 8/2014 |
| WO | 2015/083065 | 6/2015 |

OTHER PUBLICATIONS

Anonymous: "Regularization (mathematics)—Wikipedia"; Oct. 22, 2015.
(Continued)

*Primary Examiner* — Amandeep Saini
(74) *Attorney, Agent, or Firm* — Larry Liberchuk

(57) ABSTRACT

Method of data processing for Computed Tomography from a spectral image data set of an imaged zone, an anatomical image data set of the imaged zone, and an anatomical model, comprising: a. Assigning an initial set of values to a regularization scheme, 5 b. Performing a noise reduction scheme on the spectral image data set, wherein said noise reduction scheme is a function of the regularization scheme, of the spectral image data set and of the anatomical image data set, in order to obtain a processed spectral image data set, c. Performing a segmentation of structures of interest using the anatomical data set, the processed spectral image data set, and the anatomical model, in order to obtain a segmentation result, d. Updating the regularization scheme based on the segmentation result, e. Repeating step b to e, wherein the method also comprises a control step, performed when step b and c has both been performed at least once, the control
(Continued)

step comprising checking an endloop criterion, and if the endloop criterion is met, outputting at least one of the segmentation result obtained in last iteration of step c and the processed spectral image data set obtained in the last iteration of step b.

14 Claims, 5 Drawing Sheets

(51) Int. Cl.
    *G06T 5/00*     (2006.01)
    *G06T 7/00*     (2017.01)

(58) Field of Classification Search
    USPC .......................................................... 382/275
    See application file for complete search history.

(56) References Cited

U.S. PATENT DOCUMENTS

| | | |
|---|---|---|
| 2008/0205716 A1 | 8/2008 | Von Berg |
| 2010/0322489 A1 | 12/2010 | Tizhoosh |
| 2013/0053689 A1 | 2/2013 | Das |
| 2014/0133729 A1 | 5/2014 | Goshen |
| 2014/0369458 A1 | 12/2014 | Shen |
| 2015/0379694 A1* | 12/2015 | Goshen .................. A61B 6/482 |
| | | 382/195 |
| 2016/0307330 A1* | 10/2016 | Goshen ..................... G06T 7/11 |

OTHER PUBLICATIONS

Karande, et al., "Iterative Optimization Scheme for Image Segmentation"; International Journal of Computer Applications, International Conference on Recent Trends in engineering & Technology—2013.

* cited by examiner

METHOD OF DATA PROCESSING FOR COMPUTED TOMOGRAPHY

CROSS REFERENCE TO RELATED APPLICATIONS

This application is the U.S. National Phase application under 35 U.S.C. § 371 of International Application No. PCT/EP2016/079968, filed Dec. 7, 2016, published as WO 2017/102467 on Jun. 22, 2017, which claims the benefit of European Patent Application Number 15200180.6 filed Dec. 15, 2015. These applications are hereby incorporated by reference herein.

This invention relates to a method of data processing which finds particular application in Computed tomography, more specifically in spectral Computed Tomography, where signal to noise optimization limitations are inherent to this technology.

BACKGROUND OF THE INVENTION

Segmentation of anatomical and biological structures from CT images, and other imaging modalities, is a common approach in many diagnostic applications. Analyses of diseases or clinical conditions which can benefit from segmented structures can be related for example to automatic bone and calcification extraction, automatic CT angiography and vessel shape measurements, tumor lesion characterization, or differentiation between organ sections such as in cardiac, liver, or lungs.

Spectral CT can improve segmentation results in cases where better material separation or quantification adds relevant information beyond the conventional CT x-ray attenuation values, the Hounsfield Units. A known limitation of spectral CT is that usually the spectral images suffer from high noise or artifacts compared to conventional CT images. This issue sometimes leads to the application of strong non-linear filtration or other related noise reduction algorithms. Applying strong non-linear filtration sometimes degrades the spatial resolution or the low contrast resolution, and may even leave artifacts or create new image artifacts. Using such images to derive segmentation results may lead to non-optimal diagnosis.

Several techniques were proposed already to improve the noise reduction process of spectral images. These techniques were mostly based on prior information related to different tissues and material in the body.

For example, US 2013/0053689 describes a method to adjust the spectral filters in dual-energy CT based on known spectral characteristics of pre-determined tissue types, but without any relation to any organ or anatomical model. US 2008/0063135 and US2014/0133729 describe additional relevant background techniques in the field.

WO2014/128595A1 discloses a method in which spectral projection data is restored based on an underlying structure estimated from a reference dataset based on a determined noise pattern.

WO2015/083065A1 discloses a bone segmentation method for spectral image data in which a bone structure is extracted based on probabilities that were determined for each voxel if they represent a bone structure.

SUMMARY OF THE INVENTION

The current invention relates to an improved technique to adjust the noise reduction process of the spectral results based on an anatomical model, in such a way that it will optimally support and improve the desired segmentation.

In relation to the current invention, advanced segmentation algorithms often include prior shape and structural models which are dedicated to specific tissue or organ types, for example based on human anatomical atlases, or knowledge about the physical and mechanical properties of the relevant tissues. These models are very important in regulating and refining the structural information that can be inferred from the CT images which is sometimes noisy and incomplete.

More specifically, the current invention is a method of data processing for Computed Tomography from a spectral image data set of an imaged zone, an anatomical image data set of the imaged zone, and an anatomical model, comprising:

a. Assigning an initial set of values to a regularization scheme,
b. Performing a noise reduction scheme on the spectral image data set, wherein said noise reduction scheme is a function of the regularization scheme, of the spectral image data set and of the anatomical image data set, in order to obtain a processed spectral image data set,
c. Performing a segmentation of structures of interest using the anatomical data set, the processed spectral image data set, and the anatomical model, in order to obtain a segmentation result,
d. Updating the regularization scheme based on the segmentation result,
e. Repeating step b to e, wherein the method also comprises a control step, performed when step b and c has both been performed at least once, the control step comprising checking an endloop criterion, and if the endloop criterion is met, outputting at least one of the segmentation result obtained in last iteration of step c and the processed spectral image data set obtained in the last iteration of step b.

Step a initializes the regularization scheme. The noise reduction scheme of step b can be any scheme or algorithm meant to improve the background of the image by reducing the amount of unwanted information, such as noise or artifacts.

Spectral dual energy reconstruction algorithm typically consists of two main steps. First, a two-base model spectral decomposition is performed. In this step, the energy dependent attenuation profile of each material is approximated as a linear combination of two bases, e.g., the attenuation profiles of the photoelectric and Compton scattering effects in the water. In the second step, material quantification and classification are performed and the final spectral result is created, e.g., virtual monochromatic image, iodine map or VNC.

In spectral dual energy CT there is an inherent noise challenge, i.e., each of a specific energy readings is usually based on roughly half of the radiation dose of a corresponding non-spectral conventional scan reading. In addition, the spectral decomposition is an ill-posed problem, in which the noise is significantly amplified. Additionally, the obtained noise is highly negatively correlated between the bases.

Therefore, a dedicated noise removal algorithm is required to deliver robust and accurate results. This algorithm utilizes a restoration cost function that consists of the following components:

The first component is a noise model that accurately models the noise, including the negatively correlated noise pattern. Once an accurate noise model is utilized, the algorithm performed better restoration of the underlying object structures which leads to more accurate reconstructions.

The second component is the regularization. The regularization enables the algorithm to reduce the image noise by penalizing the roughness of the images. In addition, the regularization ensures robust performance by improving the numerical stability of the reconstruction process.

The third component is a spectral gradient synchronization with the conventional image. The basic idea here is that in most of the gradient locations in the base images there are also gradients in the conventional image. This observation is incorporated as a soft constraint in the reconstruction algorithm. This additional constraint improves the robustness and the accuracy of the algorithm.

The noise reduction scheme of step b outputs a processed spectral image data set. Step b can be always applied to the same initial spectral image data set, which is not updated at each iteration, with a regularization scheme which is updated at each iteration. Alternatively, step b can be applied on an updated spectral image data set, the processed spectral image data set of last iteration being reinjected into the noise reduction algorithm at each iteration. Said processed spectral image data set is used together with the anatomical data set and the anatomical model in order to obtain a segmentation result. The segmentation step consists in segmenting different structures from the imaged zone. Any known segmentation method can be used. Usually these rely on identifying discontinuities in the imaged zone which are likely not to be artifact or noise in view of the anatomical model. Based on the segmentation result, the regularization scheme can be refined as the segmentation result gives information about the locations which are likely to be susceptible to noise-reduction artifacts and about the locations which are more likely to be noisy. This updated regularization scheme can then be used to produce a new processed spectral image data set, which will allow for a better segmentation, which, in turn, will lead to a finer regularization scheme. These steps thus form a loop which can be iterated as long as needed. A control step is performed, preferably but not necessarily once per iteration, to determine when the loop should stop being iterated.

The steps a to e do not need to be executed in a subsequent order.

The control step can be performed either between step c and step d, between step d and step e, or between step b and c. That is to say the control step can be performed either before or after updating the regularization scheme based on the last segmentation results. In a preferred embodiment, the control step is performed between step b and c. This allows outputting a processed spectral image data set which takes into account the last segmentation result. However, it might be interesting to output the final segmentation result as soon as it is available, in which case it is interesting to perform the control step between step c and d.

Step d can comprise assigning a coefficient or a numerical weight to a primal region of the imaged zone, and said coefficient can depends on parts of the segmentation result associated with at least one proximate region of the imaged zone which is conterminous of the primal region. Specifically, as step d is meant to weight which parts of the image zones need to undergo noise reduction, step d can assign an important—or a low-coefficient in case of a primal region which needs little to no noise reduction.

This can be the case of a primal region which is close to an anatomical discontinuity if the noise reduction scheme consists in a smoothing algorithm which averages a region in function of the surrounding regions. That is to say, if the segmentation result identifies a primal region which is very different of a proximate, conterminous, region, then this difference should be preserved and no 'noise reduction scheme' should erase it. To materialize that, a coefficient can be assigned to the primal region. The coefficient can also depend on values taken by the anatomical image data set in the primal region and in the proximate region of the imaged zone, on the anatomical model, and/or on the presence of a material of interest in the primal region.

The segmentation results can be of any type. It can for instance consists in determining in a binary way whether a region belongs to the structures of interest. This can be materialized in assigning a value, such as '1' to a region of the imaged zone which belongs to the structures of interest and either another value, such as '0', or no value at all to a region which does not belong to the structures of interest. It is also possible to make a distinction between several structures of interest by using more than two different value. For instance, the segmentation result can assign the value '1' to a region which belongs to the wall of a vessel, the value '2' to a region which belongs to the lumen of the vessel, and the value '0' for a region which belongs to none of these structures.

The generic term region which has been employed can designate a region of any size and shape. In a preferred embodiment, the primal region has a size of one single voxel. This allows to make best use of the resolution available.

Different possible endloop criterion can be used depending on the protocol and the resources available. Typically, the endloop criterion can be met if at least two iterations of step c have been performed and at least one of the segmentation result, the processed imaged data set or the regularization scheme has not undergone a threshold of minimal total differences between the last two iterations. Alternatively, the endloop criterion can be met if step e, or any other step, has been iterated a predetermined number of time.

The method according to the invention can further comprises calculating the probability that a region of the imaged zone belongs to the structures of interest, preferably by integrating the distances between said region and boundaries of the structures of interest. This can be a clever way to refine the calculation of the previously mentioned coefficient, hence making a finer application of the noise reduction scheme.

The invention also relates to a Computed Tomography scanner configured to output an anatomical image data set and a spectral image data set out of a single scan, said anatomical image data set and said spectral image data set being provided in a format designed to be used by a method according to the invention.

Finally, the invention also relates to a Computer readable storage medium encoded with computer readable instructions, which, when executed by a processor, causes the processor to perform a method according to the invention.

BRIEF DESCRIPTION OF THE FIGURES

The invention shall be better understood by reading the following detailed description of an embodiment of the invention and by examining the annexed drawing, on which.

DETAILED DESCRIPTION OF EMBODIMENTS

Figure 1:
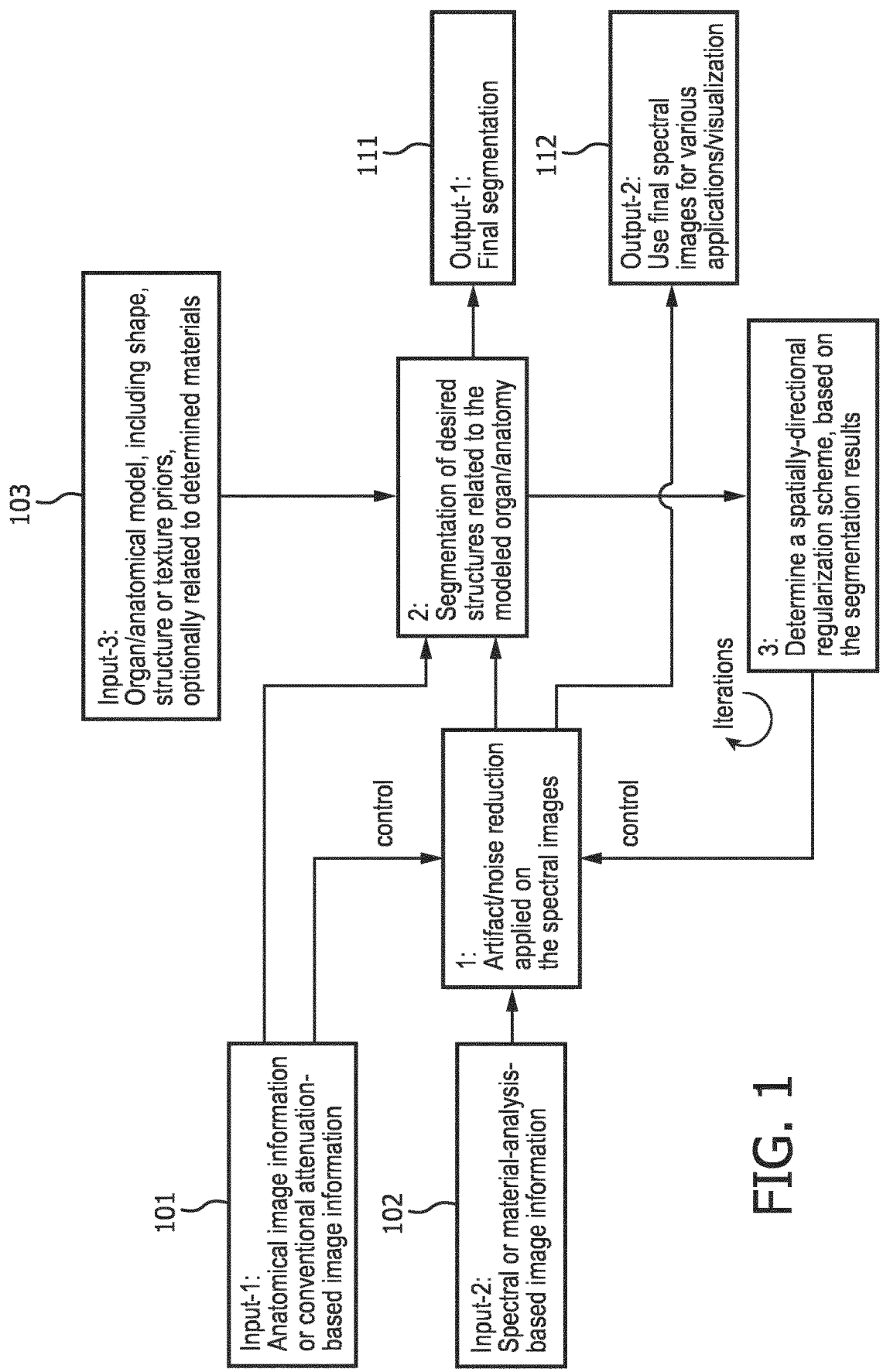
FIG. 1 is a high level flowchart of a method according to the invention.

FIG. 1 shows an overall view of a preferred embodiment according to the invention. Three types of input data are used:

a) the first input 101 is an anatomical attenuation-based image set, which is related to the images obtained through a conventional Computed Tomography scan, or to the virtual monochromatic images which are usually available in a spectral-Computed Tomography scan.

b) the second input 102 is the material-characteristics spectral-based images which are available from the multi-energy spectral-Computed Tomography data. There are several way to get these images, for example from dual x-ray tube voltage sampling, from dual detection layers, or from energy-binned photo counting detection. It is common to use for the spectral images, derived results such as photo/scatter pair, or two image sets calculated for two different monochromatic energies.

c) the third input 103 is an anatomical or organ model which includes prior information on the relevant shapes and structures but can also include prior information related to specific materials or tissues and their spectral characteristics. For example, a model can include knowledge about the bones and the skeleton, including the biological materials which tend to construct the different parts of the bones. The model may also include knowledge about blood vessel structures and arrangement, and it may determine that the modeled blood vessels include iodine which is injected in the relevant protocols.

The aim of the method according to the invention is to obtain an optimal segmentation 111 of the organ or tissue of interest and on the same hand to obtain high quality spectral results 112 for other possible clinical applications. These are the two outputs of the method according to the invention.

The segmentation process 130 is based on all three inputs 101, 102 and 103. For that purpose, known general techniques can be used such as graph-cut (a mathematical technique for image segmentation, usually consisting in using some prior knowledge on the required segment properties), K-means, active contours (a method to segment structures, usually based on some smoothness assumptions regarding the structures boundaries), level set methods and more. The segmentation process 130 is further detailed in FIG. 4.

Figure 5:
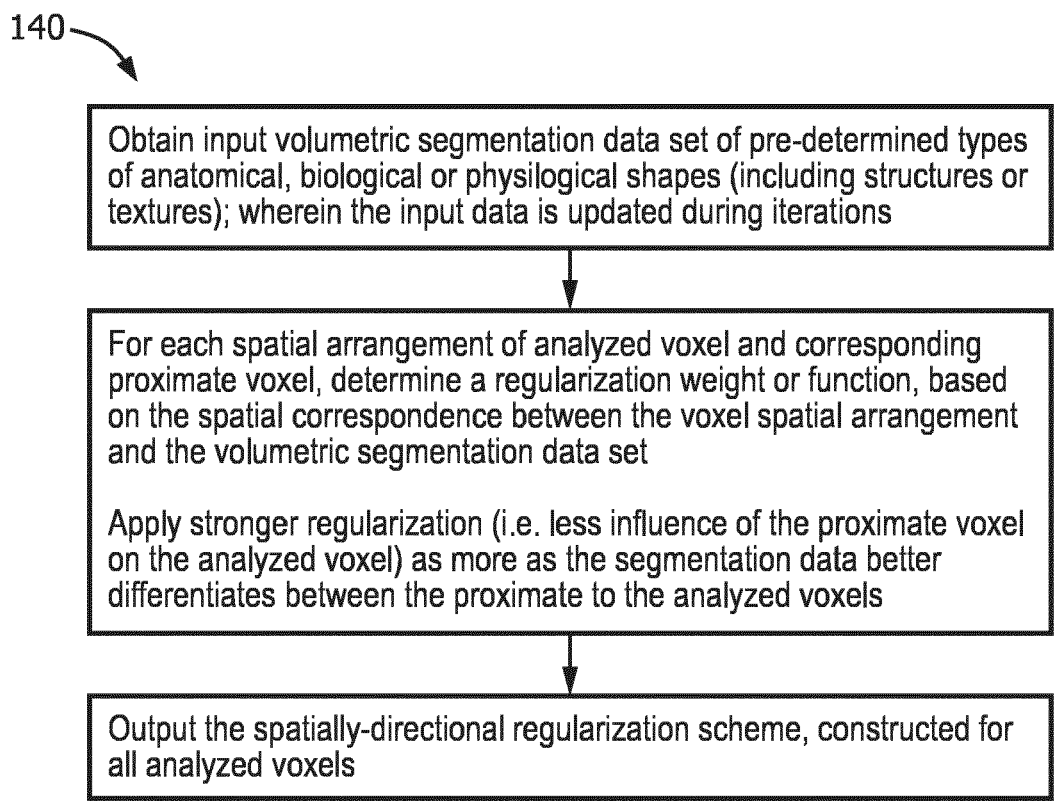

A regularization scheme 140, which is further detailed in FIG. 5 is performed out of the segmentation result of the process 130. The purpose of the regularization scheme is to determine how to apply the noise reduction process 120.

Indeed, particularly valuable information is included in the spectral data. As such, it is very important to apply correctly the noise reduction process 120, since the spectral images in spectral Computed Tomography are usually very noisy in practical clinical conditions. Artifacts in the spectral images may relate to known effects in Computed Tomography such as streaks, blooming, beam-hardening, cone-beam, and low-frequency patterns. The noise reduction step is further detailed in FIG. 3.

In order to achieve the desired goal, the adjustment of the artifact/noise reduction 120 and the calculated segmentation are performed in an iterative process, including the special regularization scheme 140. In each iteration, the regularization is based on the recent, temporary, segmentation results, and it is applied to control the filter adjustment. It is The process converges to a sufficient segmentation results after few iterations. This iterative process is a more practical solution than trying to solve a global optimization equation using the non-optimized filtered spectral images after only a single run, which is faster and demands less resources.

Figure 2:
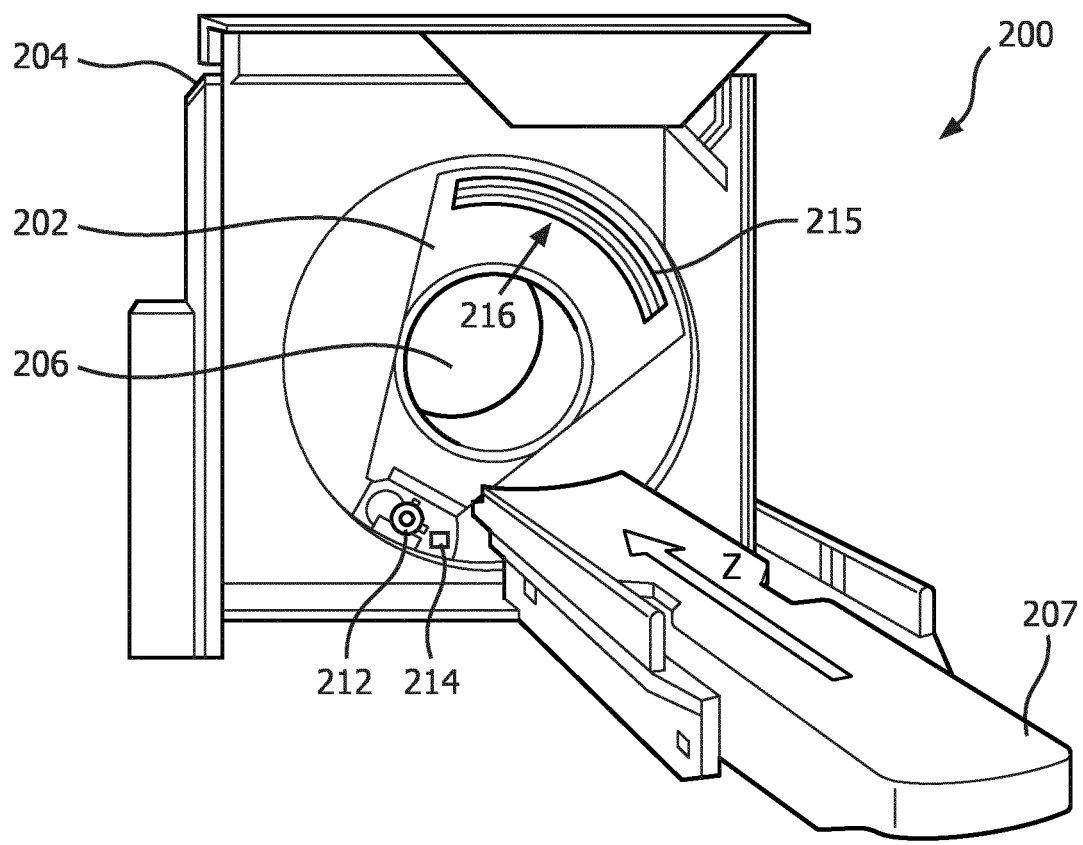
FIG. 2 represents a typical Computed Tomography scanner.

FIG. 2 schematically illustrates an example imaging system 200, such as a computed tomography (CT) scanner typically used to obtain the two first input 101 and 102 of the method according to the invention. The imaging system 200 includes a rotating gantry 202 and a stationary gantry 204. The rotating gantry 202 is rotatable supported by the stationary gantry 204. The rotating gantry 202 is configured to rotate around an examination region 106 about a longitudinal or z-axis. The imaging system 200 further includes a subject support 207 that supports a subject or object in the examination region 206 before, during and/or after scanning. The subject support 207 can also be used to load and/or unload the subject or object into or from the examination region 206. The imaging system 200 further includes a radiation source 212, such as an x-ray tube, that is rotatable supported by the rotating gantry 202. The radiation source 212 rotates with the rotating gantry 202 around the examination region 206 and is configured to generate and emit radiation that traverses the examination region 206. The imaging system 200 further includes a radiation source controller 214. The radiation source controller 214 is configured to modulate a flux of the generated radiation. For example, the radiation controller 214 can selectively change a cathode heating current of the radiation source 212, apply a charge to inhibit electron flow of the radiation source 212, filter the emitted radiation, etc. to modulate the flux.

The imaging system 200 further includes a one or two dimensional array 215 of radiation sensitive detector pixels 216. The array 215 is located opposite the radiation source 212, across the examination region 206, detect radiation traversing the examination region 206, and generate an electrical signal (projection data) indicative thereof.

Figure 3:
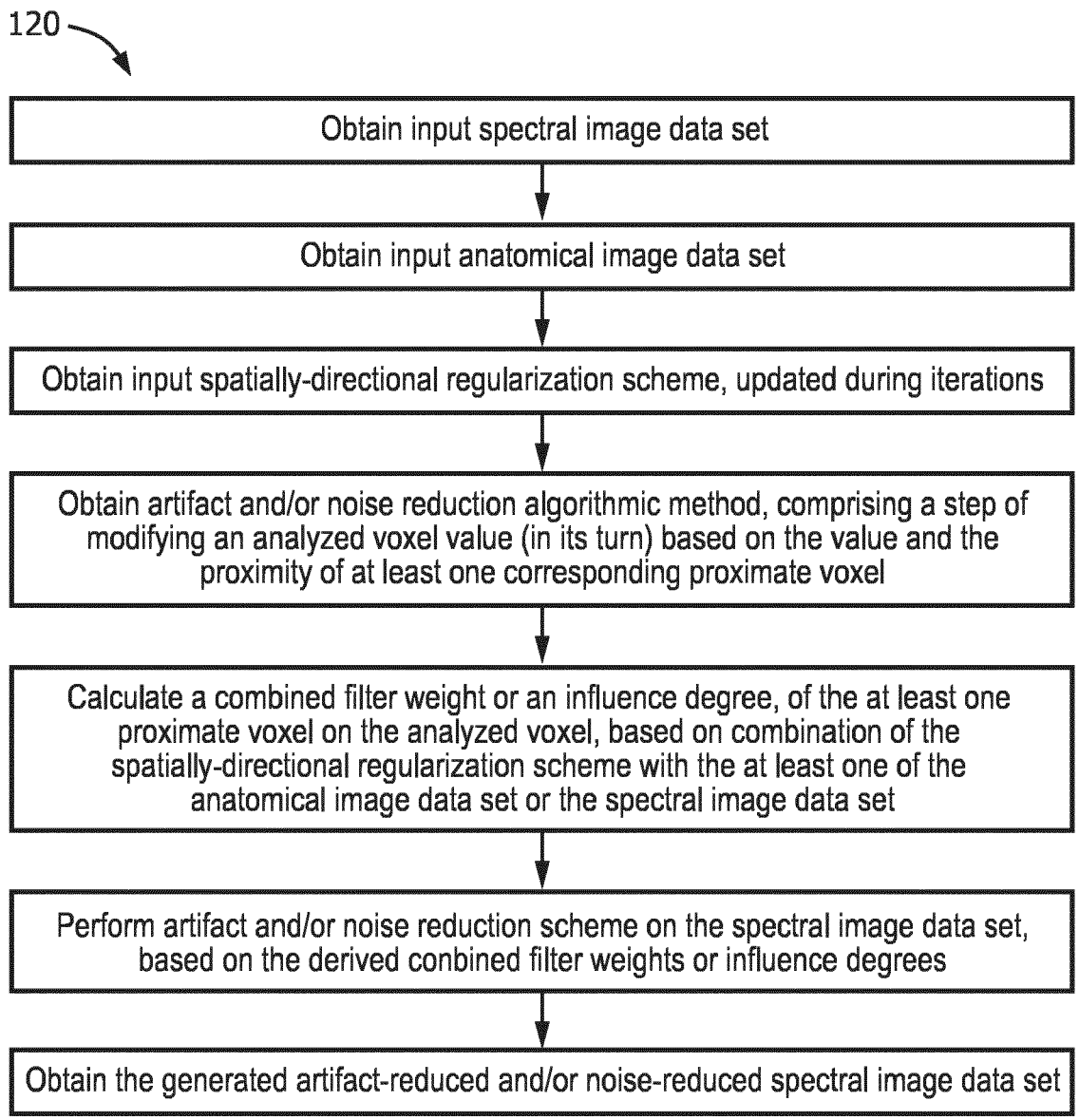
FIG. 3 is a more detailed flowchart of the noise/artefact reduction part of a method according to the invention.

FIG. 3 details the noise reduction step 120 of the method presented in FIG. 1. The input information in this step is: the spectral image data set -V; the anatomical image data set -C; and a spatially directional regularization scheme R. The regularization term R is determined for each two voxels denoted as 'a' and 'p', an analyzed and a proximate voxels respectively. For example, during the algorithm execution, the method will consider all the analyzed voxels in the specified volume, and for each such voxel a set of proximate (i.e. neighbor) voxels will be determined. In this example, the regularization is determined as a function H of the spatial coordinates of the analyzed and proximate voxels ($X_a$, $X_p$) and on the recent volumetric segmentation results -S. -$R_{ap}$=H($X_a$, $X_p$, S). For example, the segmentation representation may give the value '1' for all voxels which are belong to the desired structure (possibly of a specific material), and the value '0' for all voxels which are not belong to the desired structure.

In addition to the three specified inputs, the noise/artifact reduction algorithm is determined as:

$V_a^{new}$=F($W_{ap}^1$, ... $W_{ap}^1$, ... $R_{ap}^n$) where $V_a^{new}$ is the updated value of the analyzed voxel and F is a function depending on the regularization $R_{ap}$ corresponding to each of the proximate voxels (i=1 ... n), and on calculated weights $W_{ap}$ (for each i=1 ... n). The weights may be determined as a function—

$W_{ap}=G(X_a, X_p, V_a, V_p, C_a, C_p,)$ dependent on the values and coordinates of the analyzed and proximate voxels, and they may be also dependent on the corresponding values in the anatomic image ($C_a$, $C_p$).

In the process of noise/artifact reduction, a new value $V_a^{new}$ for each of the analyzed voxels will be determined and an updated volume of spectral image data will be generated.

For example, a simple possible form of the function F may be: $sum_i(W_{ap}^i)$, for all those i proximate voxels where $X_a$ and $X_p^i$ are in the same segment in S (and after proper normalization of the weights).

Another option for example is that the weight $W_{ap}^i$ is partially modified as a function of the distances between $X_a$ and/or $X_p^i$ to the boundaries of the segmented structure, in order to create the combined weight.

Figure 4:
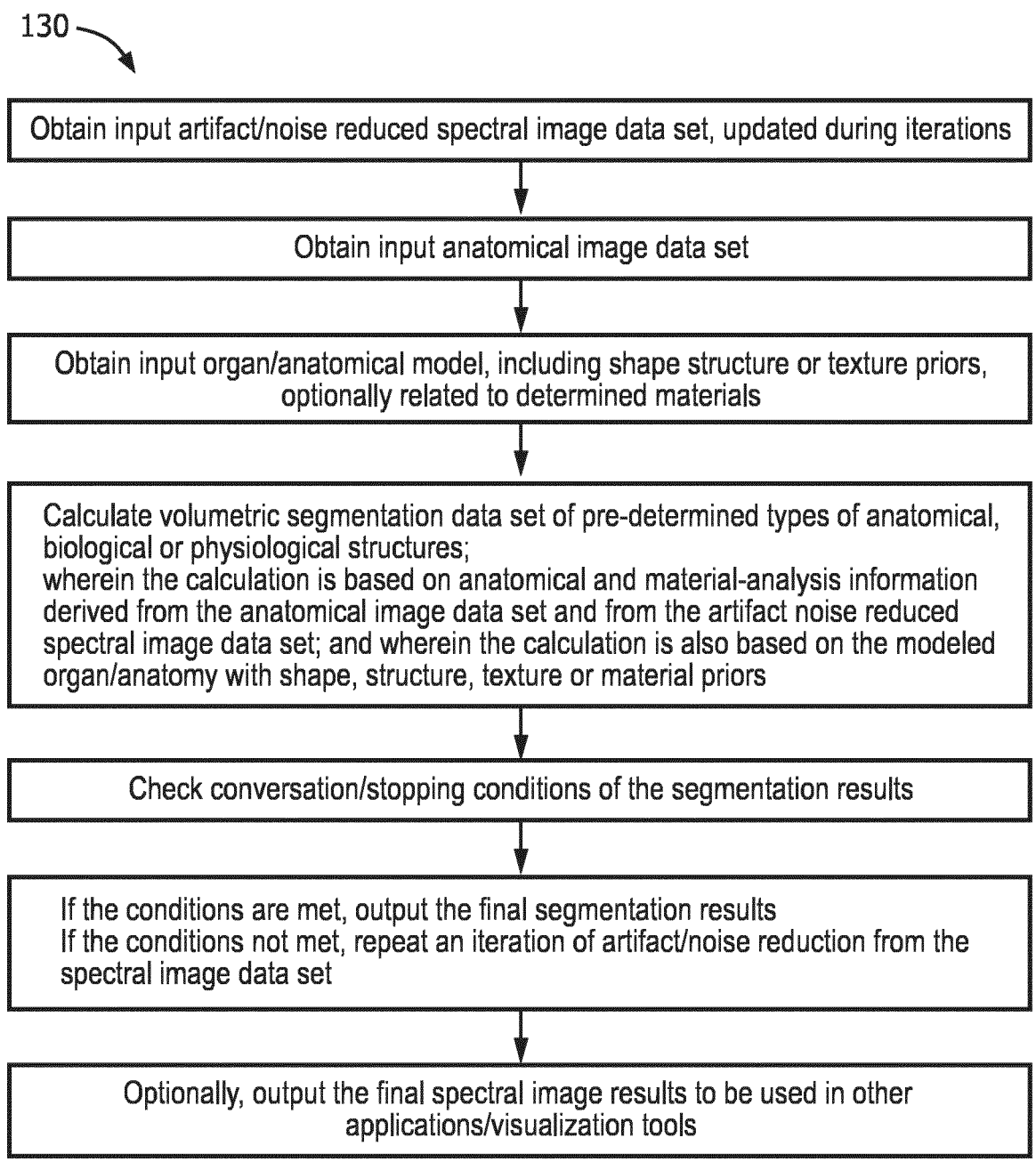
FIG. 4 is a more detailed flowchart of the segmentation part of a method according to the invention and, FIG. 5 is a more detailed flowchart of the regularization part of a method according to the invention.

FIG. 4 details a possible way of performing the segmentation step 130 of the method of FIG. 1.

This flowchart performs the segmentation of the desired structures based on the three input information sets. The input spectral image data set is improved by selective noise and artifact reduction through repeated iterations.

After each iteration, a new segmentation volume is generated. This result is checked relative to the previous segmentation results and according to pre-determined convergences or stopping conditions. Based on that it is determined whether the iterations should be stopped and, eventually, the final segmentation volume is output. For example, the convergence condition may be based on a threshold for the minimal total differences between successive iteration results, or it can be based on a pre-determined number of iterations.

FIG. 5 details the regularization step 140 of the method illustrated in FIG. 1.

As described in FIG. 3, the spatially directional regularization scheme can be determined as $R_{ap}=H(X_a, X_p, S)$, where the regularization R is determined for each two voxels denoted as a and p, an analyzed and a proximate voxels respectively. In this example, the regularization is determined as a function H of the spatial coordinates of the analyzed and proximate voxels ($X_a$, $X_p$) and on the recent volumetric segmentation results—S.

Here, the meaning of 'regularization' is that the noise/artifact reduction step is operated in a reduced strength where the regularization is high (corresponding to both position and direction in the volume). That is to say, a high regularization suppresses locally the noise reduction operation. One resultant effect is that mostly the relevant edges and boundaries between different materials are preserved.

In general, the regularization strength will be higher if the two voxels (the analyzed and the proximate) are in two different parts of the segmentation volume (e.g. one is belong to the segmented structure and the second is not belong to the segmented structure). In addition, the regularization strength will be higher if the two voxels, in the two different segmentation parts, are relatively far from the segment boundaries (and therefore the probability that they indeed belong to different parts is higher).

Alternatively, if the analyzed and the proximate voxels are well within the same part of the segmentation volume, the regularization will be low or zero.

In an embodiment of the invention, the probability that a voxel (either the analyzed or the proximate) belongs to a segmentation part is calculated by integrating the distances between the voxel to the segmented structure edges in all relevant directions. This can provide higher accuracy in determining the directional regularization in cases where the segmented structure edges are highly curved or non-uniform.

The regularization may also be material-dependent, based on the model. For example, a model of specific blood vessel arrangement (e.g. related to specific organ) may refer only to iodine contrast agent. In such way, the spectral filter regularization will apply to those voxels which are spectrally analyzed as including iodine, and will not be applied to voxels which contain other materials. This approach may better delineate, for example, small plaque regions in arteries.

It is also possible that the model will include different structures in relation to different materials (e.g. iodine, calcium, fat, soft-tissue, air, brain white and gray matter, tendons and ligaments, uric-acid, etc.). The structures that are derived from the spectral images can particularly reinforce the segmentation accuracy of such modeled material-specific structures.

While the invention has been illustrated and described in detail in the drawings and foregoing description, such illustration and description are to be considered illustrative or exemplary and not restrictive; the invention is not limited to the discussed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A computer implemented method of data processing for Computed Tomography from a spectral image data set of an imaged zone, an anatomical image data set of the imaged zone, and an anatomical model, comprising:
   a. Assigning an initial set of values to a regularization scheme,
   b. Performing a noise reduction scheme on the spectral image data set, wherein said noise reduction scheme is a function of the regularization scheme, of the spectral image data set and of the anatomical image data set, in order to obtain a processed spectral image data set,
   c. Performing a segmentation of structures of interest using the anatomical data set, the processed spectral image data set, and the anatomical model, in order to obtain a segmentation result,
   d. Updating the regularization scheme based on the segmentation result,
   e. Repeating step b to e,
   wherein the method also comprises a control step, performed when step b and c have both been performed at least once, the control step comprising checking an endloop criterion, and if the endloop criterion is met, outputting at least one of the segmentation result obtained in the last iteration of step c and the processed spectral image data set obtained in the last iteration of step b.

2. The method according to claim 1, wherein the control step is performed between step c and step d.

3. The method according to claim 1, wherein the control step is performed between step d and step e.

4. The method according to claim 1, wherein step d comprises assigning a coefficient to a primal region of the imaged zone.

5. The method according to claim 4, wherein said coefficient depends on parts of the segmentation result associated with at least one proximate region of the imaged zone which is conterminous of the primal region.

6. The method according to claim 4, wherein said coefficient depends on the anatomical model.

7. The method according to claim 4, wherein the coefficient depends on the presence of a material of interest in the primal region.

8. The method according to claim 1, wherein the coefficient also depends on values taken by the anatomical image data set in the primal region and in the proximate region of the imaged zone.

9. The method according to claim 1, wherein the segmentation results consists in determining in a binary way whether a region belongs to the structures of interest.

10. The method according to claim 1, wherein the primal region has a size of one single voxel.

11. The method according to claim 1, wherein the endloop criterion is met if at least two iterations of step c have been performed and at least one of the segmentation result, the processed imaged data set or the regularization scheme has not undergone a threshold of minimal total differences between the last two iterations.

12. The method according to claim 1, wherein the endloop criterion is met if step e has been iterated a predetermined number of time.

13. The method according to claim 1 further comprising calculating the probability that a region of the imaged zone belongs to the structures of interest, preferably by integrating the distances between said region and boundaries of the structures of interest.

14. A non-transitory computer readable storage medium encoded with computer readable instructions, which, when executed by a processor, causes the processor to perform a method according to claim 1.

* * * * *